(12) United States Patent
Andermahr et al.

(10) Patent No.: US 9,757,172 B2
(45) Date of Patent: Sep. 12, 2017

(54) SYSTEM AND METHOD FOR MINIMALLY INVASIVE CLAVICLE PLATE APPLICATION

(71) Applicant: DePuy Synthes Products, Inc., Raynham, MA (US)

(72) Inventors: Jonas Andermahr, Marmagen (DE); Flora Mauch, Zuerich (CH); Claudia Reichle, Langendorf (CH); Philipp Brun, Basel (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 15/334,056

(22) Filed: Oct. 25, 2016

(65) Prior Publication Data

US 2017/0035478 A1   Feb. 9, 2017

Related U.S. Application Data

(63) Continuation of application No. 12/694,953, filed on Jan. 27, 2010, now Pat. No. 9,486,262.

(51) Int. Cl.
*A61B 17/80* (2006.01)

(52) U.S. Cl.
CPC ........ *A61B 17/8061* (2013.01); *A61B 17/809* (2013.01); *A61B 17/8057* (2013.01)

(58) Field of Classification Search
CPC . A61B 17/80; A61B 17/8061; A61B 17/8057; A61B 17/809
See application file for complete search history.

(56) References Cited

U.S. PATENT DOCUMENTS

| 4,573,458 | A  | 3/1986  | Lower |
| 8,118,846 | B2 | 2/2012  | Leither et al. |
| 2004/0204713 | A1 | 10/2004 | Abdou |
| 2007/0185493 | A1 | 8/2007  | Feibel et al. |
| 2007/0213726 | A1 | 9/2007  | McGarity et al. |
| 2007/0233106 | A1 | 10/2007 | Horan et al. |

*Primary Examiner* — Christopher Beccia
(74) *Attorney, Agent, or Firm* — Fay Kaplun & Marcin, LLP

(57) ABSTRACT

A bone fixation plate, comprises an elongated body contoured to conform to the anatomy of a clavicle, the elongated body comprising a head at a first end and a shaft extending therefrom to a second end, the second end further comprising a reduced diameter tapered tip configured to permit insertion of the elongate body through a minimally invasive incision formed adjacent the clavicle. The bone fixation plate also comprises a first plate hole extending through the shaft from a proximal face to a distal face, the first plate hole formed as a combination hole and a second plate hole extending through the head from the proximal face to the distal face, the second plate hole being threaded.

20 Claims, 5 Drawing Sheets

SYSTEM AND METHOD FOR MINIMALLY INVASIVE CLAVICLE PLATE APPLICATION

The present application is a Continuation Application of U.S. patent application Ser. No. 12/694,953 filed on Jan. 27, 2010, now U.S. Pat. No. 9,486,262. The entire disclosure of this patent/application is expressly incorporated herein by reference.

BACKGROUND

Clavicle fractures are the second most frequently occurring fractures in humans. Osteosynthesis procedures at the clavicle shaft generally require the insertion of a bone plate through an incision approximately 10-15 cm, in length. The size of the incision presents numerous complications including post-operative scarring and irritative complications arising from contact of the procedure site with items of clothing, backpacks, etc. Furthermore, current clavicle fixation procedures employ Recon plates, which often do not provide adequate stability to a fractured clavicle, sometimes requiring the insertion of a second bone plate to achieve the required stability.

SUMMARY OF THE INVENTION

The present invention is directed to a bone fixation plate comprising an elongated body contoured to conform to the anatomy of a clavicle, the elongated body comprising a head at a first end and a shaft extending therefrom to a second end, the second end further comprising a reduced diameter tapered tip configured to permit insertion of the elongate body through a minimally invasive incision formed adjacent the clavicle. The bone fixation plate also comprises a first plate hole extending through the shaft from a proximal face to a distal face, the first plate hole formed as a combination hole and a second plate hole extending through the head from the proximal face to the distal face, the second plate hole being threaded.

DETAILED DESCRIPTION

The present invention is directed to a system and method for minimally invasive fixation of clavicle fractures in living bodies. Specifically, the present invention is directed to a system including a bone plate having a plurality of angled bone plate holes and combination plate holes configured to permit an angled inserted of bone screws therethrough. As described in more detail below, a first exemplary bone plate according to the present invention comprises an elongated body with a lateral extension at a first end thereof where a width of the lateral extension (i.e., an extent of the lateral extension in a direction substantially perpendicular to a longitudinal axis of the elongated body) is greater than the width of the elongated body. A second end of this bone plate comprises a tapered tip configured to minimize trauma to adjacent soft tissue as the bone plate is guided through the minimally invasive incision to a target position against the clavicle. In an exemplary embodiment, the minimally invasive incision is approximately 1-3 cm, in length and, in a preferred embodiment, is approximately 2 cm long. A second exemplary bone plate according to the present invention includes an elongated body without any lateral extensions, wherein the elongated body has a uniform width and tapered tips at both ends thereof, as will be described in greater detail hereinafter. As used in this application, the term proximal refers to a direction approaching a physician or other user of the device and the term distal refers to a direction along the device extending away from the user. In an operative configuration, a distal face of the bone plate of the present invention is seated against the clavicle while the proximal face faces away from the clavicle.

Figure 1:
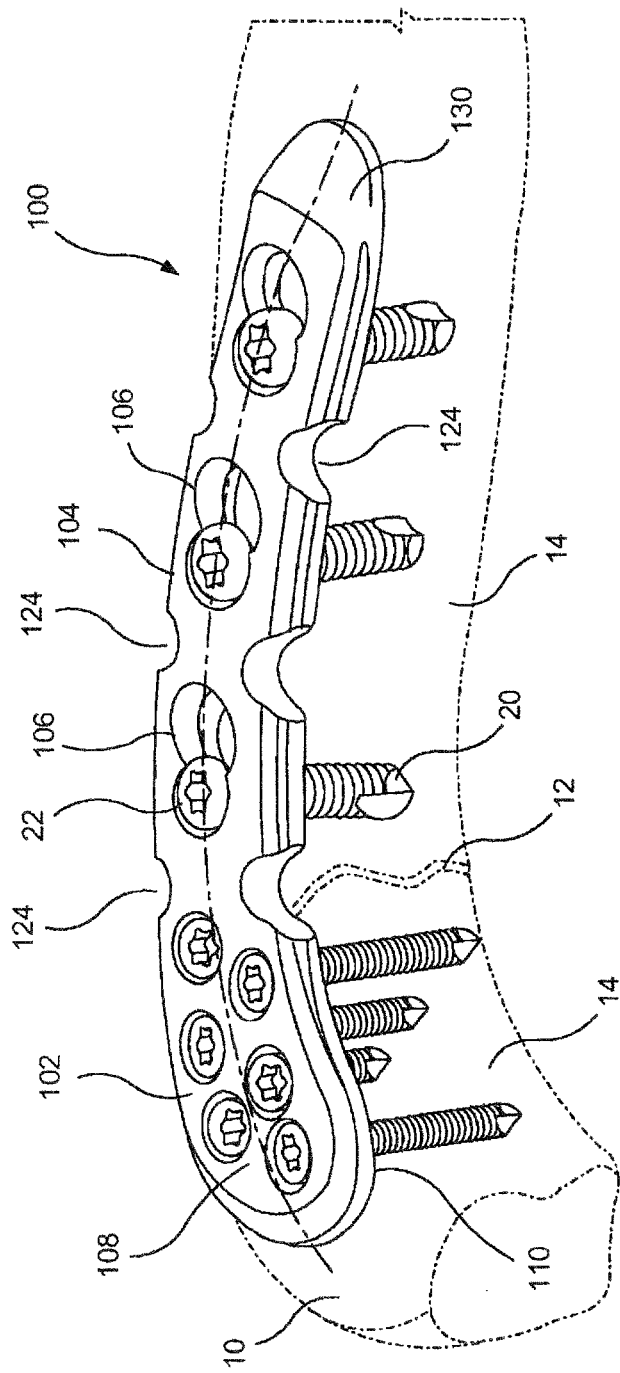
FIG. 1 shows a first perspective view of a bone plate according to a first embodiment of the present invention positioned against a clavicle.
Figure 3:
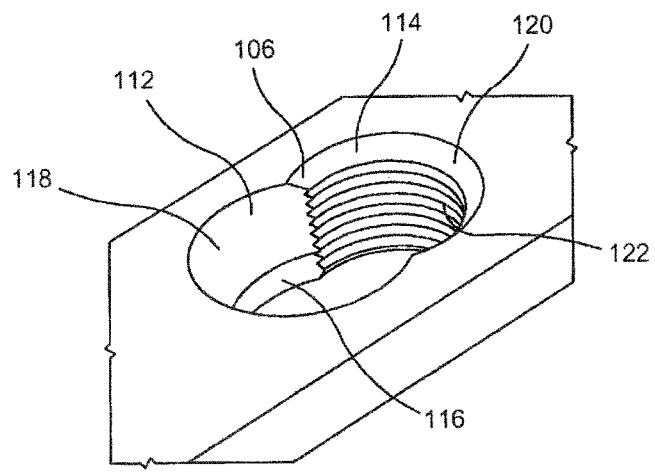
FIG. 3 shows a zoomed perspective view of a plate hole of the bone plate of FIG. 1.

FIG. 1 shows a bone plate 100 according to a first exemplary embodiment of the invention. The bone plate 100 is an elongated element comprising a lateral extension 102 at a first end and a shaft 104 of substantially uniform width extending therefrom in a second direction. However, those skilled in the art will recognize that the plate 100 may be formed in any dimensions suitable to the patients anatomy. The shaft 104 comprises a plurality of fixation element holes 106 extending therethrough from a proximal face 108 to a distal face 110 which, when the plate 100 is applied to a bone in a desired configuration, faces the bone 10. The holes 106 are spaced from one another along a longitudinal axis of the shaft and extend substantially along a centerline of the bone plate 100. In an exemplary embodiment, at least 2 of the plate holes 106 are combination holes with a first substantially circular hole 112 overlapping a second substantially circular hole 114 and open to each other. In a preferred embodiment, a diameter of the first hole 112 is substantially equivalent to a diameter of the second hole 114, with the diameter of the second hole 114 being selected to threadedly engage the threaded head of a bone screw 20 inserted therethrough. In a preferred embodiment, each of the first and second holes 112, 114 are approximately 3.5 mm. in diameter. The first hole 112 may be formed with a smooth outer wall with a substantially cylindrical portion 116 extending perpendicularly from the proximal face 108 to the distal face 110. As shown in greater detail in FIG. 3, the first hole 112 also comprises a tapered portion 118 extending distally thereinto from the proximal face 108 by a predetermined distance. The tapered portion 118 has a greater diameter than the cylindrical portion 116 to permit an angularly stable insertion of the bone screw 20 into the plate hole 106 while also seating a head 22 of the bone screw 20 therein, as will be described in greater detail later on. The second hole 114 comprises a tapered portion 120 extending distally from the proximal face 106 by a predetermined distance to a substantially cylindrical threaded portion 122.

Figure 2:
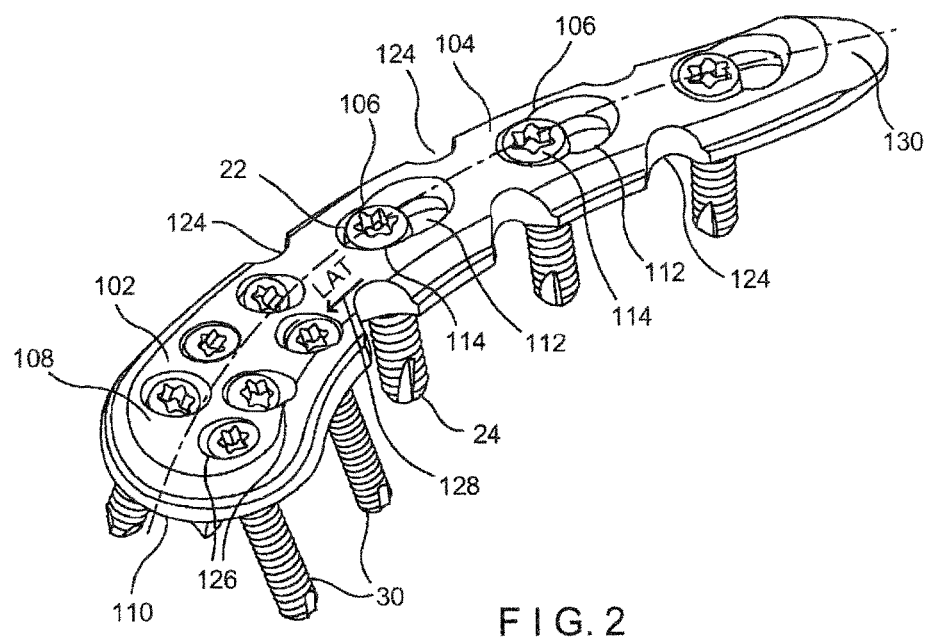
FIG. 2 shows a second perspective view of the bone plate of FIG. 1.

Those skilled in the art will understand that the use of a combination plate hole 106 offers the advantage of permitting selective use of a compression screw or an angularly stable locking screw by inserting the bone screw 20 into either the first hole 112 or the second hole 114. Specifically, the bone screw 20 may be inserted through the first hole 112 at an angle suited to the dimensions of the bone 10 and the location of a fracture 12 thereof to maximize dynamic-axial compression. Alternatively, the bone screw 20 may be inserted through the second hole 114 at an angle relative to an axis of the second hole 114 selected by the user so that the screw head 22 is stably seated with a threaded portion thereof threadedly engaging the cylindrical portion 122 and screwed into the bone 10 without a loss of reduction. Thus the user can select the angle of insertion of the bone screw 20 to ensure good bony purchase to the bone screw 20 to stabilize a bone with multifragment fractures or osteoporotic bone. It is noted that although only three bone plate hole 106 are shown in the present embodiment, any number of bone plate holes 106 may be employed in the shaft 104 without deviating from the scope of the present invention. A length of the bone plate 100 along the longitudinal axis thereof may range from approximately 69 mm. when three plate holes 106 are used to approximately 135 mm. when 8 plate holes are used, although it is noted that any other combination of dimensions and quantity of plate holes 106 may be employed without deviating from the scope of the present invention as dictated, for example, by the anatomy of the patient being treated. The exemplary bone plate shown in FIGS. 1-2 is configured for positioning over an anterior face of a left clavicle. As would be understood by those skilled in the art, the dimensions and orientation of the bone plate 100 may be varied as necessary to suit the anatomy of a particular patient and/or of a particular part of the clavicle being treated. For example, if the procedure is being performed on an anterior face of a right clavicle, the positions of the lateral extension 102 and the shaft 104 may be reversed so that the shaft 104 lies medial to the lateral extension 102 in an operative configuration. The bone plate 100 may also be provided with a positioning inscription 128 to indicate any or all of a proper position on the clavicle for which the bone plate 100 is suited as well as a desired orientation of the bone plate 100 on the target portion of the clavicle, as those skilled in the art will understand. Specifically, the positioning inscription 128 may comprise an arrow and a textual indicator with a proper orientation of the bone plate 100 being indicated by, for example, an upright position of the textual indicator. The positioning inscription 128 may be located anywhere on the bone plate 100 without deviating from the scope of the present invention.

The shaft 104 also comprises a plurality of arc-shaped cutouts 124, cross-sectional shapes thereof resembling a part of a circle. The cut-outs 124 are configured to allow any necessary plate contouring by defining weakened portion of the bone plate 100 which may be bent as needed to conform the shape of the bone plate 100 to a shape of the bone 10, as will be described in greater detail later on. In an exemplary embodiment, the cut-outs 124 are located between adjacent ones of the plate holes 106. In addition, the bone plate 100 may be formed with a rounded profile to prevent trauma to adjacent soft tissue when implanted on the bone 10. Specifically, as shown in FIGS. 1 and 2, an outer perimeter of the bone plate 100 and a cross-sectional profile of the bone plate 100 are substantially rounded. In addition, the distal face 110 may be provided with undercuts (not shown) to reduce an area of contact between the bone plate 100 and the bone 10, thus reducing the impairment of blood supply, as those skilled in the art will understand, The lateral extension 102, which, as described earlier has a width (i.e., an extent in a direction perpendicular to the longitudinal axis of the plate 100) greater than that of the shaft 104, is configured for placement over a lateral end of the clavicle 10. That is, the lateral extension 102 is shaped and positioned so that, when the plate 100 is placed on the bone 10 in a desired location, the lateral extension 102 overlies a target region of the lateral end of the clavicle 10 with a plurality of lateral plate holes 126 distributed along two axes extending substantially parallel to the longitudinal axis of the bone plate 100. It is noted however that the lateral plate holes 126 may be distributed over the lateral extension 102 in any other desired pattern without deviating from the scope of the present invention. The lateral plate holes 126 are preferably 2.4 mm. or 2.6 mm. in diameter. Each of the lateral plate holes 126 extends through the lateral extension 102 from the proximal face 108 to the distal face 110 along a hole axis angled with respect to a perpendicular to the distal face 110 so that a bone screw 30 inserted therein passes into the bone 10 along a desired line. Specifically, angles of the lateral plate holes 126 of this embodiment are selected so that bone screws 30 inserted therethrough diverge away from the longitudinal axis of the bone plate 100. The lateral plate holes 126 may comprise threads configured to lockingly engage threading formed on the heads of the bone screws 30, as those skilled in the art will understand. Furthermore, angles of the lateral plate holes 126 may be selected to ensure ample screw purchase in the bone 10 while increasing a pull-out strength thereof, wherein any angles may be employed that permit the bone screw to extend through the bone 10 without extending out of an opposing face of the bone 10.

The shaft 104 terminates at a tapered distal tip 130 which facilitates percutaneous insertion of the bone plate 100 minimizing irritation of soft tissue between the incision and the target location on the bone. In an exemplary embodiment of the present invention, the bone plate 100 may be used for fractures of the lateral clavicle, malunions of the lateral clavicle and non-unions of the lateral clavicle. The length of the bone plate 100 may be adjusted when treating a clavicle with a shaft fracture, as those skilled in the art will understand.

In accordance with an exemplary method according to the present invention, a minimally invasive incision approximately 1-2 cm. in length is formed over a medial sternal end of the fractured clavicle 10. An assessment is made to determine a required plate length and required bone screw positions as would be understood by those skilled in the art. Due to variations in anatomy, the bone plate 100 may require bending to seat on the clavicle 10 in a desired manner.

Figure 6:
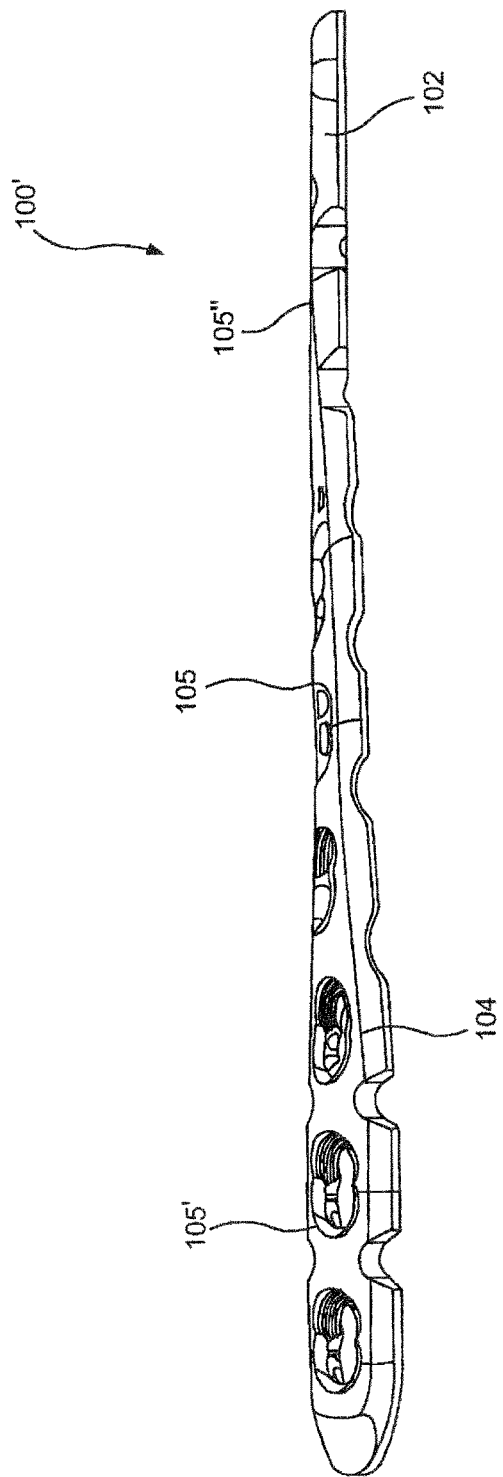
FIG. 6 shows a perspective view of the bone plate of FIG. 1 after being twisted by a bending rod.

To facilitate this bending, bending irons (not shown) may be used to contour the bone plate 100 as needed at one or more of the cutouts 124. It is noted that the bending irons (not shown) may be used to form a twist at any location along the length of a bone plate 100'. In one embodiment, as shown in FIG. 6, the shaft 104 may be provided with a twist 105 so that a plane housing a distal portion 105 of the shaft 104 is offset from a plane housing a proximal portion 105", an offset of the two planes being selected to permit the bone plate 100' to be seated over a target portion of bone.

In one embodiment of the invention, a locking compression plate ("LCP") drill sleeve (not shown) may be inserted into at least one of the plate holes 106 and/or lateral plate holes 126 to prevent damage to threads thereof during bending, as those skilled in the art will understand. After the bone plate 100 has been contoured, the positions of bone screws 20, 30 inserted through the plate hole 106 and lateral plate holes 126 may be checked under image intensification to pre-operatively plan the fixation of the bone 10. The bone plate 100 is then inserted into the incision, for example, using the LCP drill sleeve as a handle. The bone plate 100 is positioned over the clavicle 10 in a desired position and fragments 14 are brought into a desired alignment with one another. An image intensifier known in the art may be used to ensure proper bone alignment, as those skilled in the art will understand.

Figure 4:
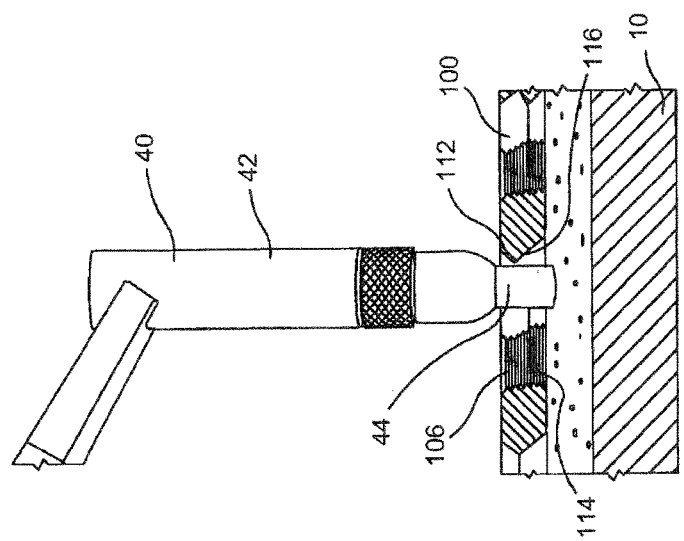
FIG. 4 shows a drill guide for forming a bore in a bone according to a first method of the present invention.
Figure 5:
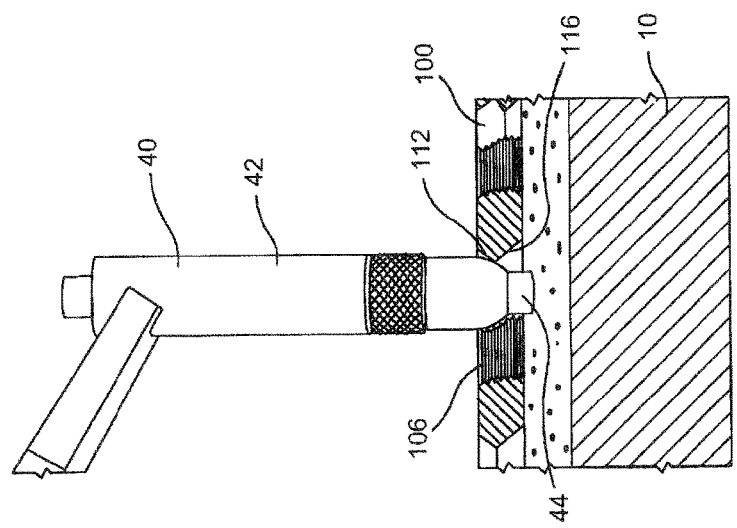
FIG. 5 shows a drill guide for forming a bore in a bone according to a second method of the present invention.

A physician or other user then determines the type of bone screws 20, 30 to be used in the bone plate 100, the selection being dependent on the anatomy of the bone 10 and the location of the fracture 12. In one embodiment, Kirschner wires may be inserted through the plate holes 106 and lateral plate holes 126 prior to the insertion of bone screws 20, 30 to verify the final intended screw positions. The Kirschner wires then removed prior to insertion of the bone screws 20, 30. As shown in FIGS. 4-5, a universal drill guide 40 may then be used to guide the insertion of the bone screw 20, 30 into the respective plate holes 106 and lateral plate holes 126. The drill guide 40 is formed as an elongated cylindrical shaft 42 with a reduced diameter tip 44 at a distal end thereof spring loaded to retract into the shall 42 upon application of a predetermined pressure. In an exemplary embodiment, the drill guide 40 may be used to pre-drill 2.5 mm. holes at desired angles into the bone 10 at the desired locations. For insertion of locking screws in the lateral plate holes 126, the drill guide 40 is inserted through the lateral plate hole 126 and seated against the bone so that the tip 44 is retracted into the shaft 42. A drill bit (not shown) is then inserted through the drill guide 40 to drill a bore into the bone 10 to a desired depth, avoiding contact between the drill bit and the subclavian artery and brachial plexus, as those skilled in the art will understand. The drill guide 40 may be provided with a scale to determine a required length of the bone screw 30. This ensures that the selected bone screw 30 does not go entirely through the bone 10 and damage blood vessels and soft tissue inferior to the clavicle. The bone screws 30 which, in a preferred embodiment are 2.7 or 2.4 mm. screws, are then screwed into the lateral plate holes 126 either manually or using a powered insertion. It is noted that although a universal drill guide 40 is shown, any other drill guide known in the art may be employed with the exemplary system and method of the present invention, including, but not limited to, a threaded 3.5 mm locking hole drill guide, as those skilled in the art will understand.

Once all the required bone screws 30 have been inserted into the lateral extension 102, bone screws 20 may be inserted into the plate holes 106 in substantially the same manner as described above. Depending on the requirements of the procedure being performed (e.g., based on a fracture pattern), the bone screw 30 may be inserted into the lateral extension 102 either prior to or after the insertion of the bone screws 20 into the plate holes 106. If a neutral position of the bone screw 20 is desired in the plate hole 106, the drill guide 40 may be pressed into first hole 112 so that the tip 44 is retracted into the shaft 42. A bore (not shown) formed by the drill 40 is spaced from outer walls of the plate hole 106 due to the increased diameter of the shaft 42 relative to the tip 44 so that the bone screw 20 is properly guided into the bore without compressing the bone plate 100 during insertion. If a compression position of the bone screw 20 is desired, the drill guide 40 is positioned so that the tip 44 is not compressed into the shaft 42 (i.e., with the tip 44 seated contacting a wall of the first hole 112) so that the bone screw 20 inserted through this bore contacts walls of the first hole 112. In this manner, an eccentrically pre-drilled bore guides an bone screw 20 into the bone at an angle such that the fracture and bone plate 100 are compressed. After the target bores have been drilled into the bone 10, a depth gauge (not shown) may be inserted through the drill guide 40 to determine a required bone screw length, as those skilled in the art will understand. The 3.5 mm bone screws 20 are then inserted into the bone 10. If locking screws are to be inserted into the second hole 114 of the plate hole 106, the same procedure described above is followed with a threaded drill guide being threaded into the second hole 114 while pre-drilling a bore into the bone and the head of each bone screw 20 being threadedly screwed into the corresponding second hole 114 until the head is seated flush against the tapered portion 120.

To remove the bone screws 20, 30 and the bone plate 100 from the bone 10 (e.g., after the bone 10 has healed), each of the bone screws 20, 30 is first unscrewed from the bone 10 a predetermined distance so that removal of the bone screws 20, 30 does not cause a rotation of the bone plate 100 over the bone which may damage adjacent soft tissue. Once unlocked from the bone 10, the bone screws 20, 30 are individually removed from the body and the bone plate 100 is then removed through a minimally invasive incision. It is further noted that the exemplary method of the present invention may be used with any other bone plate for insertion into a living body, including, but not limited to substantially planar bone plates including LCP plates and reconstruction plates, as those skilled in the art will understand.

Figure 7:
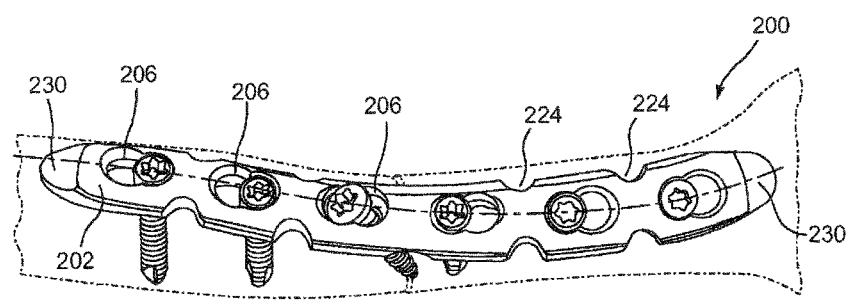
FIG. 7 shows a perspective view of a bone plate according to a second embodiment of the present invention.

As shown in FIG. 7, a bone plate 200 according to an alternate embodiment of the invention is formed substantially similarly to the bone plate 100 of FIG. 1 except that an elongated body 202 thereof includes no lateral extensions 102. The bone plate 200 comprises plate holes 206 formed substantially similarly to the plate holes 106 and a plurality of arc-shaped cutouts 224 substantially similar to the cutouts 124. The body 202 of the bone plate 200 is provided with contouring and curvatures selected to conform to one of a right clavicle and a left clavicle in the same manner described above for the plate 100. Furthermore, the bone plate 200 may be further contoured by a physician to conform to the anatomy of a particular patient as described earlier. Furthermore, the bone plate 200 may be configured for one of lateral superior placement over the clavicle or for medial anterior placement thereover. Ends of the bone plate 200 may be provided with tapered tips 230 facilitating insertion thereof into the body with a minimal amount of tissue irritation irrespective of which end is introduced into the body first. The bone plate 200 may be inserted into the body and locked onto the clavicle in the same manner described above with respect to the bone plate 100.

Figure 8:
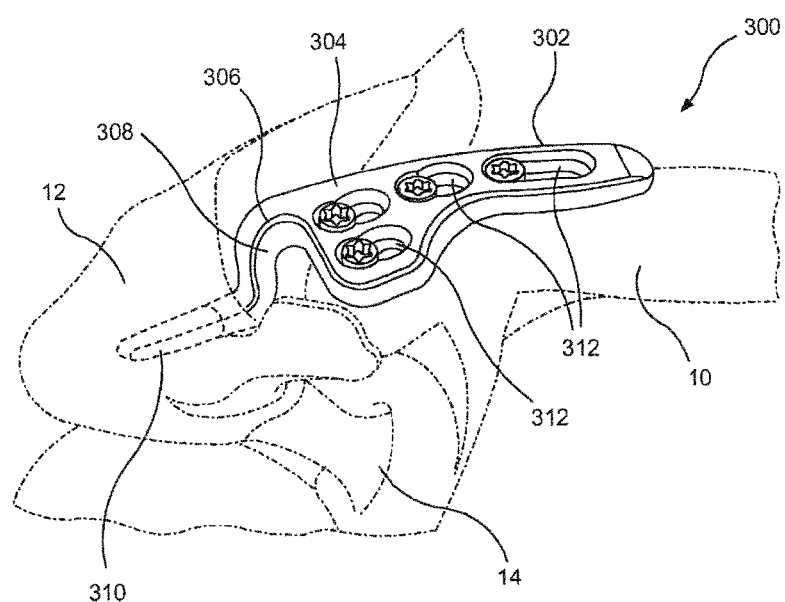
FIG. 8 shows a perspective view of a bone plate according to a third embodiment of the present invention.

As shown in FIG. 8, a bone plate 300 according to another embodiment of the invention is configured for the fixation of acromioclavicular ("AC") joint dislocation and fractures of the left clavicle. It is noted however that the bone plate 300 may also be configured for the fixation of the right clavicle by mirroring the positions of the components described hereinafter. Specifically, the bone plate 300 comprises a shaft 302 including an increased diameter lateral extension 304 at a first end thereof. The shaft 302 is configured to rest on a shaft of the clavicle 10 while the lateral extension 304 rests laterally thereof, closer to the AC joint. The bone plate 300 also comprises a hook 306 with a first portion 308 extending inferior to the lateral extension 304 and a second portion 310 extending laterally toward the acromion 12 of the scapula 14, as those skilled in the art will understand. The shaft 302 and lateral extension 304 further comprise a plurality of plate holes 312 which may be a combination of combination plate holes and circular plate holes extending from a proximal face of the bone plate 300 to a distal face thereof at any angle suited to the requirements of a target bone fixation procedure distributed and oriented in the same manner described above.

Although the present invention has been described with reference to preferred embodiments, it is submitted that various modifications can be made to the exemplary system and method without departing from the spirit and scope of the invention.

What is claimed is:

1. A method for treating a bone in a living body, comprising:
   cutting a minimally invasive incision into a portion of skin located adjacent one of a medial and lateral end of a clavicle;
   manipulating fragments of the clavicle to achieve a desired spatial relationship therebetween;
   inserting a bone plate through the minimally invasive incision, the bone plate being an elongated body contoured to conform to the anatomy of a clavicle, the elongated body comprising a head at a first end and a shaft extending therefrom to a second end, the second end further comprising a reduced diameter tapered tip configured to permit insertion of the elongate body through the minimally invasive incision, a first plate hole extending through the shaft from an outer surface which, in use, faces away from the clavicle to a bone facing surface thereof which, in use, faces the clavicle, the first plate hole being formed as a combination hole, and a second plate hole extending through the head from the outer surface to the bone facing surface, the second plate hole being threaded; and
   inserting bone screws through the first and second plate holes into the clavicle to secure the bone plate to the clavicle.

2. The method of claim 1, further comprising the step of contouring the bone plate to conform to the shape of the clavicle prior to insertion in the body.

3. The method of claim 1, further comprising the steps of:
   inserting a drill guide into one of the first and second plate holes, the drill guide comprising an elongated hollow cylindrical body formed with a retractable reduced-diameter cylindrical distal tip; and
   inserting a drill through the drill guide to form a bore in the bone, the bore guiding screwed insertion of the bone screws into the bone.

4. The method of claim 1, further comprising the step of:
   applying a distally directed force on the drill guide to retract the distal tip into the cylindrical body, and to seat a distal rim of the cylindrical body against the bone, wherein engagement of the cylindrical body with a wall of one of the first and second plate holes positions the bore to extend from the wall.

5. The method of claim 1, further comprising the step of positioning the drill guide so that the distal tip abuts a wall of one of the first and second plate hole to position the bore against the wall.

6. The method of claim 2, wherein the bone plate comprises a plurality of arced cutouts formed along an outer perimeter of the elongated body, the cutouts being formed as parts of a circle.

7. The method of claim 6, wherein the bone plate is contoured to the shape of the clavicle by bending the bone plate at one or more of the cutouts.

8. The method of claim 1, wherein the second plate hole extends from the outer surface to the bone facing surface at an angle that is not perpendicular to the outer surface.

9. The method of claim 1, wherein the bone plate comprises a positioning marking indicating proper insertion orientation of the bone plate.

10. The method of claim 1, further comprising the step of inserting a depth gauge through the drill guide to determine a required bone screw length.

11. A method for treating a bone in a living body, comprising:
    cutting a minimally invasive incision into a portion of skin located over a medial sternal end of a clavicle;
    inserting a bone plate through the incision, the bone plate having an elongated body contoured to conform to the anatomy of a clavicle, the elongated body comprising a head at a first end and a shaft extending therefrom to a second end, the second end further comprising a reduced diameter tapered tip configured to permit insertion of the elongate body through the incision, a first plate hole extending through the shaft from an outer surface which, in use, faces away from the clavicle to a bone facing surface which, in use, faces the clavicle, the first plate hole being formed as a combination hole, and a second plate hole extending through the head from the outer surface to the bone facing surface, the second plate hole being threaded, the head including a lateral extension disposed between the first end and the second end, the lateral extension being contoured to rest on a target region of a lateral end of the clavicle, the lateral extension having a width greater than a substantially uniform width of the shaft;
    inserting a drill guide into one of the first and second plate holes to form a bore in the bone; and
    inserting bone screws through the first and second plate holes into the clavicle.

12. The method of claim 11, wherein the drill guide comprises an elongated hollow cylindrical body formed with a retractable cylindrical distal tip.

13. The method of claim 12, further comprising the step of applying a distally directed force on the drill guide to retract the distal tip into the cylindrical body to seat a distal rim of the cylindrical body against the clavicle, engagement of the cylindrical body with a wall of one of the first and second plate holes positions the bore to extend from the wall.

14. The method of claim 11, further comprising the step of positioning the drill guide so that the distal tip abuts a wall of one of the first and second plate holes to position the bore against the wall.

15. The method of claim 11, further comprising the step of contouring the bone plate to conform to the shape of the clavicle prior to insertion in the body.

16. The method of claim 15, wherein the bone plate comprises a plurality of arced cutouts formed along an outer perimeter of the elongated body, the cutouts formed as parts of a circle.

17. The method of claim 15, wherein the bone plate is contoured using a bending iron.

18. The method of claim 11, further comprising removing the bone screws and the bone plate from the clavicle after the bone has healed.

19. The method of claim 18, further comprising:
    unscrewing each of the bone screws a predetermined distance;
    individually removing each of the bone screws from the bone plate; and
    removing the bone plate from the body through the incision.

20. The method of claim 11, wherein the bone plate includes a positioning marking indicating a proper insertion orientation of the bone plate.

\* \* \* \* \*